United States Patent
Nishimae et al.

(10) Patent No.: US 7,741,426 B2
(45) Date of Patent: Jun. 22, 2010

(54) METHOD FOR PRODUCTION OF FLUORINATED PHENYLENEDIAMINE

(75) Inventors: Shinji Nishimae, Kyoto (JP); Go Masuda, Suita (JP); Yasunori Okumura, Kobe (JP)

(73) Assignee: Nippon Shokubai Co., Ltd, Osaka (JP)

( * ) Notice: Subject to any disclaimer, the term of this patent is extended or adjusted under 35 U.S.C. 154(b) by 82 days.

(21) Appl. No.: 10/561,048

(22) PCT Filed: Jun. 21, 2004

(86) PCT No.: PCT/JP2004/009049

§ 371 (c)(1),
(2), (4) Date: Dec. 14, 2005

(87) PCT Pub. No.: WO2004/113267

PCT Pub. Date: Dec. 29, 2004

(65) Prior Publication Data

US 2006/0142539 A1   Jun. 29, 2006

(30) Foreign Application Priority Data

Jun. 23, 2003  (JP) ............... 2003-177730

(51) Int. Cl.
C08G 69/08 (2006.01)
(52) U.S. Cl. ..................... 528/310; 564/335
(58) Field of Classification Search ............. 564/335; 528/310
See application file for complete search history.

(56) References Cited

U.S. PATENT DOCUMENTS

| 3,461,135 A | | 8/1969 | Gosnell | |
|---|---|---|---|---|
| 3,897,498 A | * | 7/1975 | Zengel et al. | 564/414 |
| 5,011,997 A | * | 4/1991 | Hazen et al. | 564/335 |
| 5,410,082 A | * | 4/1995 | Pfirmann | 564/414 |

FOREIGN PATENT DOCUMENTS

| CA | 2123242 | 11/1994 |
|---|---|---|
| EP | 0 120 575 A1 | 10/1984 |
| EP | 6001914 | 1/1994 |
| EP | 1 275 679 A1 | 1/2003 |
| JP | B-47-6294 | 2/1972 |
| JP | 60-112751 | 6/1985 |
| JP | B-63-5023 | 2/1988 |
| JP | A-6-239810 | 8/1994 |
| JP | A-7-70007 | 3/1995 |
| JP | 2001-226329 | 8/2001 |

OTHER PUBLICATIONS

Andrews et al., "Aromatic Amides VI Proton Magnetic Resonance Spectra of Some 2-Substituted 1,3-Phenylenediamines and their N,N'-Diacyl Derivatives" Aust. J. Chem., No. 24, 1971,pp. 413-422.
Harvey et al., "o-Nitroaniline Derivatives. Part 1 1. 4- and 7-Amino-1H-benzimidazole 3-Oxides" J. Chem Soc. Perkin Trans., vol. 7, No. 7, Jul. 1988, pp. 1939-1943.
"Synthesis of fluoride compound and function" CMC K.K., May 6, 1987, pp. 204-205.
Harvey et al., "o-Nitroaniline Derivatives. Part 11. 4- and 7- Amino-1H-benzimidazole 3-Oxides," J. Chem Soc. Perkin Trans. I, No. 7,pp. 1939-1943 (1988).

* cited by examiner

*Primary Examiner*—James Seidleck
*Assistant Examiner*—Gregory Listvoyb
(74) *Attorney, Agent, or Firm*—Occhiuti Rohlicek & Tsao LLP

(57) ABSTRACT

A method for the production of a fluorinated phenylenediamine is provided which comprises steps of reacting a diamide represented by the following formula with NaOCl at a molar ratio of the NaOCl to the diamide in the range of 2.0-6.0 and NaOH at a molar ratio of the NaOH to the diamide in the range of 1.8-6.0 is provided. According to this invention, the fluorinated phenylenediamine can be produced conveniently in a high yield.

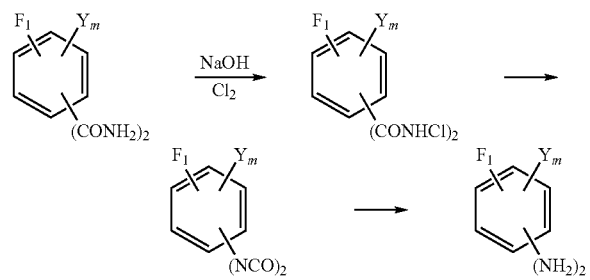

17 Claims, No Drawings

METHOD FOR PRODUCTION OF FLUORINATED PHENYLENEDIAMINE

CROSS-REFERENCE TO RELATED APPLICATIONS

This application is the National Stage of International Application No. PCT/JP2004/009049, filed Jun. 21, 2004, which claims the benefit of Japanese Patent Application Serial No. 2003-177730, filed on Jun. 23, 2003. The contents of both of the foregoing applications are hereby incorporated by reference in their entity.

TECHNICAL FIELD

This invention relates to a method for the production of a novel fluorinated phenylenediamine and more particularly to a method for producing a fluorinated phenylenediamine in a high yield under moderate reaction conditions by a simple process.

BACKGROUND ART

A fluorinated phenylenediamines such as tetrafluoro-m-phenylenediamine is an important intermediate for the synthesis of pharmaceutical preparations, pesticides, and macromolecular compounds, and is particularly useful as a raw material for a fluorine-containing polyimide having a low dielectric constant and a low refractive index, absorbing light sparingly, and having excellent water repellency.

Tetrafluoro-m-phenylenediamine, for example, has been heretofore produced by the ammonolysis of hexafluorobenzene or pentafluoroaniline or by a process of reacting pentafluoroaniline with such a nucleophilic reagent as phthalic imide which can add an amino group thereby inducing the substitution of an amino group for the fluorine atom and then converting the fluorine atom into the amino group. For example, Example 3 of U.S. Pat. No. 3,461,135 discloses a method for producing tetrafluoro-m-phenylenediamine by reacting pentafluoroaniline with phthalimide potassium and redistilled dimethyl formamide, adding ethanol and hydrazine to the mixture, refluxing the resultant reaction solution, and subsequently adjusting the pH of the refluxed product with sodium hydroxide to a weak alkali. This method, however, produces tetrafluoro-m-phenylenediamine in such a low yield as 13.4% and, by-produces tetrafluoro-p-phenylenediamine which is an isomer thereof as well as the tetrafluoro-m-phenylenediamine. As mentioned above, when tetrafluoro-m-phenylenediamine is to be produced, tetrafluoro-p-phenylenediamine is generally by-produced simultaneously at an approximate ratio in the range of 8: 2 to 9:1.

The tetrafluoro-m-phenylenediamine aimed at, therefore, must be separated and purified as by a process of distillation, recrystallization, column chromatography, and sublimation, for example. It is, however, extremely difficult to separate and purify the tetrafluoro-m-phenylenediamine and the by-produced tetrafluoro-p-phenylenediamine from each other.

JP-B-47-6,294 discloses a method for separating and purifying tetrafluoro-m-phenylenediamine, which comprises acylating crude tetrafluoro-m-phenylenediamine containing tetrafluoro-p-phenylenediamine thereby precipitating the m-isomer in the form and subjecting the residual filtrate further to diacylation and hydrolysis, and separating the m-isomer in the filtrate in the diacylated form. This method also requires to involve a process of separation and purification or tetrafluoro-m-phenylenediamine.

Another known method for producing tetrafluoro-m-phenylenediamine comprises reacting tetrachloroisophthalonitrile in a benzonitrile medium with a fluorinating agent at a temperature in the range of 190-400° C. under spontaneous pressure (JP-B-63-5,023) thereby producing tetrafluoroisophthalonitrile, transforming this product to the form of a diamide (tetrafluoroisophthalamide), and subjecting the resultant tetrafluoroisophthalamide to Hoffmann rearrangement ("Synthesis of fluoride compound and function," pp. 204-205, published by CMC K.K. on May 6, 1987).

Yet another known method for producing tetrafluoro-m-phenylenediamine comprises reacting tetrafluoroisophthalic acid with sodium azide in a strong acid thereby producing tetrafluoro-m-phenylenediamine (JP-A-2001-226,329). In Example 2 thereof, tetrafluoro-m-phenylenediamine is produced in a high yield of 74.0%. In Comparative Example 1 of this official gazette, a method for obtaining tetrafluoro-m-phenylenediamine which comprises using tetrafluoroisophthalamide as a raw material, adding sodium hydroxide and bromide thereto thereby converting the group, —$CONH_2$, into a group, —CONHBr, extracting the resultant compound with isopropyl alcohol, and hydrolyzing the extract by the addition of hydrochloric acid is described. This method comprises causing a mixed solution of sodium hydroxide and bromine to act on the amide moiety of tetrafluoroisophthalamide thereby converting the amide into an amine by Hoffmann rearrangement and eventually obtaining tetrafluoro-m-phenylenediamine. The yield of this product is 13.8%.

Since the Hoffmann rearrangement which is effected in the method described above uses a strong alkali such as sodium hydroxide in an excess amount, however, the fluorine atoms are partially converted into a hydroxyl group. On other words, as described in detail in Comparative Example 1, the Hoffman rearrangement in a strong acid entails the problem of lowering the yield of tetrafluoro-m-phenylenediamine as the target product.

DISCLOSURE OF THE INVENTION

Although the method described in Example 2 of the JP-A-2001-226,329 can attain a high yield, it gives rise to by-products copiously and necessitates a subsequent intense purification process. Thus, a method by which tetrafluoro-m-phenylenediamine can be produced with a high selectivity in a high yield without forming by-products, namely without entailing a process for separation and purification has been enthusiastically demanded. The tetrafluoro-m-phenylenediamine, when containing by-products only in a small amount, manifests a small molar absorption coefficient in a visible region and is particularly useful as an optical material. Therefore, a method for the production of such tetrafluoro-m-phenylenediamine having a small molar absorption coefficient in a visible region has been demanded. Moreover, a strong need has been felt for a method which permits the production of tetrafluoro-m-phenylenediamine by a moderate and simple process.

The present inventors, as a result of studying various methods for the production of tetrafluoro-m-phenylenediamine, have found that by the Hoffmann rearrangement which converts an amide into an amine by causing a mixed solution of sodium hydroxide and chlorine to act on the amide, tetrafluoro-m-phenylenediamine can be produced from tetrafluoroisophthalamide, and by adjusting the amounts of sodium hydroxide and chlorine to be formulated in the above method, the yield can be enhanced and the occurrence of by-products can be repressed extremely, and thus the subsequent process for purification can be simplified, and the produced tetrafluoro-m-phenylenediamine can enjoy high purity. This invention has been perfected as a result.

According to this invention, simply by reacting a compound as a raw material with NaOH and NaOX supplied in prescribed amounts, a fluorinated phenylenediamine represented by the formula (2) shown herein below can be produced in a high yield. The amount of NaOH to be used for the reaction is smaller as compared with the amount contemplated hitherto and the reaction, therefore, excels in safety.

In this invention, particularly by varying the temperature at two stages, the target compound can be produced while repressing the occurrence of by-products without necessitating isolation of any intermediate.

The compound obtained consequently has an extremely low molar absorption coefficient in a visible region, which indicates the occurrence of by-products as impurities only in a small amount and permits the subsequent purifying step to be simplified. Further, since this compound has high purity, it can be effectively used particularly for optical applications.

BEST MODE OF CARRYING OUT THE INVENTION

According to a first aspect of this invention, a method for the production of a fluorinated phenylenediamine represented by the following formula (2), which comprises steps of reacting a diamide represented by the following formula (1) with NaOX [wherein X stands for a bromine atom (Br) or a chlorine atom (Cl)] at a molar ratio of the NaOX to the diamide (NaOX/diamide ratio) in the range of 2.0-6.0 and with NaOH at a molar ratio of the NaOH to the diamide (NaOH/diamide ratio) in the range of 1.8-6.0.

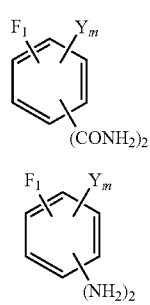

wherein in the formulas (1) and (2), Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent, l is an integer in the range of 1-4, m is an integer in the range of 0-3, provided that the total number of l and m (l+m) is 4.

This invention is aimed at producing a diamine represented by the formula (2) as the target compound by subjecting a diamide represented by the formula (1) to the so-called Hoffmann rearrangement which eliminates carbon dioxide and forms an amine by the action of a mixed solution of sodium hydroxide and chlorine. In this invention, attention has been directed to the fact that NaOCl is easily formed from a mixed solution of sodium hydroxide and chlorine. Further, they have minutely studied about the relationship between the amount of NaOCl and the amount of residual NaOH relative to the diamide represented by the formula (1) and the action of NaOCl and NaOH in the Hoffmann rearrangement, to find that by reacting the diamine with NaOX in such an amount as to give an NaOX/diamide ratio in the range of 2.0-6.0 and NaOH in such an amount as to give an NaOH/diamide ratio in the range of 1.8-6.0, a fluorinated phenylenediamine represented by the formula (2) can be produced in a high yield. In this invention, it can be contemplates that a diamine of the formula (2) is formed from a diamide of the formula (1) by the following reaction, wherein X in the formulas stands for Cl. In the following formula, Y, m, and l are as defined in the formula (1).

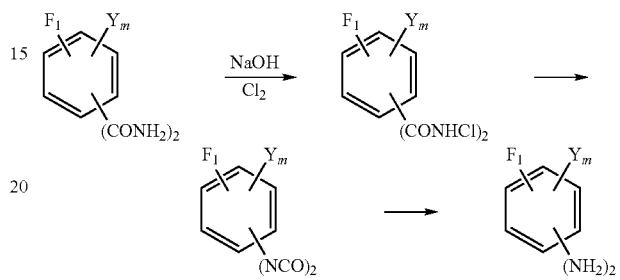

Specifically, a chlorine gas introduced into NaOH forms NaOCl, which reacts with —$CONH_2$ to substitute a chlorine atom for the hydrogen atom of the amino group and to form a —CONHCl group. Subsequently, the —CONHCl group is converted into a —NCO group following the rearrangement, which —NCO group is then hydrolyzed to form a —$NH_2$ group. This invention, therefore, is to provide a method for obtaining a fluorinated phenylenediamine represented by the formula (2) which comprises reacting the diamide with NaOX at a NaOX/diamide ratio in the range of 2.0-6.0 and NaOH at a NaOH/diamide ratio in the range of 1.8-6.0 thereby forming a compound represented by the following formula (3) and subsequently hydrolyzing this compound following the reaction of rearrangement. In the formula (3), Y, m, and l are as defined in the formula (1) and X is derived from the NaOX used in the reaction. Now, this invention will be explained in detail below.

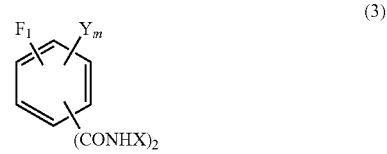

In the compound of the formula (1) and the compound of the formula (2) as the product which are used in this invention, m represents a number of Y's bound to the benzene ring, which is an integer in the range of 0-3, preferably 0 or 1. l represents a number of fluorine atoms bound to the benzene ring, which is an integer in the range of 1-4, preferably an integer in the range of 2-4, and particularly preferably 3 or 4. In this case, the total number of l and m is 4 (l+m=4). When m is 2 or 3, namely when a plurality of Y's are present, the Y's may be identical with one another or different from one another.

The diamide represented by the formula (1) to be used particularly preferably in this invention is a diamide which represented by the following formula (4).

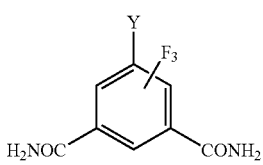

(4)

In the above formula (4), Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent, preferably F or Cl. In this preferable embodiment, a fluorinated phenylenediamine represented by the following formula (5) wherein Y is F or Cl can be produced as the fluorinated phenylenediamine represented by the formula (2).

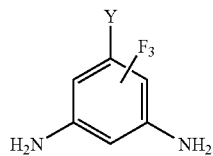

(5)

This invention is characterized by the fact that the diamide represented by the formula (1) is reacted with NaOX at a NaOX/diamide ratio (as reduced to moles) in the range of 2.0-6.0, preferably 3.0-5.0, and particularly preferably 3.5-4.5 and NaOH at a NaOH/diamide ratio (as reduces to moles) in the range of 1.8-6.0, preferably 2.0-4.0, and particularly preferably 2.0-3.0. If the NaOX/diamide ratio is less than 2.0, the yield would be lowered. Conversely, if this ratio exceeds 6.0, the amount of by-products formed would increase to make the product easily colored. Particularly, since the diamine represented by the formula (1) contains at least one fluorine atom therein, it has a possibility of hydroxylating the fluorine atom on the benzene ring with an alkali and consequently increasing the amount of by-products formed. In consideration of this possibility, this invention has set the upper limit of the NaOH/diamide ratio at 6.0. Conversely, if the NaOH/diamide ratio is less than 1.8, the shortage would be at a disadvantage in lowering the yield.

The NaOX in the form of an anhydrous salt is an extremely unstable compound. When a bromine gas or a chlorine gas is introduced into an aqueous sodium hydroxide solution, sodium hypochlorite is formed in an aqueous solution containing sodium chloride in accordance with the reaction of the following formula (6), which has been well-known.

$$Cl_2 + 2NaOH = NaOCl + NaCl + H_2O \quad (6)$$

This invention, therefore, does not need to limit to the direct introduction of NaOX into the reaction system but may also use the NaOX prepared from NaOH and a bromine gas or a chlorine gas. The latter case is preferable in terms of stability of NaOX. Incidentally, the amount of NaOX to be formed can be calculated from the amount of the bromine or chlorine gas introduced. In this invention, the NaOX/diamide ratio and NaOH/diamine ratio as mentioned above can be satisfied by adjusting the amount of NaOH and the amount of bromine gas or chlorine gas added to the diamide of the formula (1). For the purpose of reacting the diamide represented by the formula (1) with 2 mols of NaOX and 4 mols of NaOH, for example, 2 mols of bromide gas or chlorine gas may be introduced into 8 mols of an aqueous NaOH solution. Since the relationship between the occurrence of hydroxylation on the benzene ring and the amount of sodium hydroxide has hitherto remained unknown, it has been customary to have 1 mol of the diamide react with 12 mols of sodium hydroxide and 2.5 mols of bromine, namely 2.5 mols of NaOX and 7.0 mols of NaOH have been acted on 1 mol of the diamide, as demonstrated in Comparative Example 1 cited in JP-A-2001-226,329. The reaction has resulted in forming by-products copiously and conspicuously lowering the yield to a level of 13.8%. On the other hand, simply by controlling the amount of NaOH and the amount of NaOX in the aforementioned ranges, this invention can improve the yield significantly.

This invention can select other conditions in wide ranges so long as it comprises a step of reacting the compound of the formula (1) with NaOX and NaOH in both amounts falling in each the range as mentioned above. The reaction is preferably performed at a temperature in the range of 0-20° C., more preferably 0-10° C., and particularly preferably 0-5° C. It is inferred that the addition of NaOX and NaOH induces the substitution of the X of the NaOX for the hydrogen atom of the amide (—COHN₂) to efficiently form an intermediate having —CONHX represented by the formula (3). Since the compound represented by the formula (3) is extremely unstable, it is proper to perform the above reaction at a temperature of not higher than 20° C. in order to prevent the compound from being decomposed. A temperature falling short of 0° C. is not proper for the reaction because the reaction solution freezes at such a low temperature. Generally, the reaction time may be sufficiently in the range of 0.5-3 hours, preferably 1-2 hours, and more preferably 1-1.5 hours.

Subsequently, the —CONHX group in the intermediate is thermally rearranged into a —NCO group in the reaction solution to form an isocyanate represented by the following formula (7).

In this invention, the isocyanate represented by the formula (7) may be isolated from the reaction solution as by extracting the reaction solution with such a solvent as isopropyl ether and expelling the solvent by distillation by means of an evaporator before the next process. As typical examples of the solvent which is usable herein, halogenated hydrocarbons such as chloroform, methylene chloride, carbon tetrachloride, chloroethane, dichloroethane, trichloroethane, and tetrachloroethane; hydrocarbons such as pentane, hexane, cyclohexane, and heptane; aromatic hydrocarbons such as benzene, toluene, and xylene, and ethers such as diethyl ether, isopropyl ether, tetrahydrofuran (THF), dioxane, diphenyl ether, benzyl ether, and tert-butyl ether may be cited.

The isocyanate compound represented by the following formula (7) is converted into a fluorinated phenylenediamine represented by the formula (2) by the hydrolysis with an acid or an alkali. In the formula (7), Y, m, and l are as defined in the formula (1).

(7)

The acid used to act on the compound of the formula (7) is preferred to be a strong acid. As typical examples of the acid, concentrated sulfuric acid, trichloroacetic acid, sulfuric acid, polyphosphoric acids such as pyrophosphoric acid, triphosphoric acid, trimethaphosphoric acid, and tetrametaphosphoric acid, trifluoroacetic acid, trifluoroacetic anhydride, hydrochloric acid, fuming sulfuric acid, concentrated hydrochloric acid, hydrobromic acid, propionic acid, formic acid, nitric acid, and acetic acid; and the mixtures thereof such as, for example, trifluoroacetic acid-trifluoroacetic anhydride (the mixing ratio by weight in the range of 1:9-9:1, preferably 3:7-7:3), and the mixed solution of trichloroacetic acid and sulfuric acid (the mixing ratio by weight in the range of 1:9-9:1, preferably 3:7-7:3) may be cited. These acids may be used either singly or in the form of a mixture of two or more members. Among other acids cited above, at least one member selected from the group consisting of concentrated sulfuric acid, polyphosplhoric acid, trifluoroacetic acid-trifluoroacetic anhydride, trichloroacetic acid, hydrochloric acid, concentrated hydrochloric acid, and sulfuric acid, particularly concentrated sulfuric acid and/or polyphosphoric acid, is used particularly advantageously.

The amount of the acid to be used does not need to be particularly restricted but is only required to be sufficient for hydrolyzing the —NCO of the formula (7) into —$NH_2$. Generally, it is in the range of 1.8-6.0 mols, preferably 2.0-3.0 mols, per mol of the intermediate of the formula (7). If this amount is less than 1.8 mols, the hydrolysis would be attained incompletely to lower the yield. If it exceeds 6.0 mols, the excess would possibly result in adding to the amount of by-products formed.

Properly, the reaction is performed at a temperature exceeding 20° C. and not exceeding 100° C., preferably in the range of 40-80° C., and particularly 60-80° C. If this temperature is not more than 20° C., the hydrolysis would be prevented from being completed or the rate of reaction would be lowered, to impair the productivity. Conversely, if the temperature exceeds 100° C., the amount of by-products formed would increase to lower the selectivity. The reaction time may be in the range of 0.5-3 hours, preferably 0.5-2 hours, and more preferably 1-1.5 hours.

When the compound of the formula (7) is hydrolyzed with an acid, the resultant compound of the formula (2) may possibly exist in the form of an acid adduct. In the present specification, therefore, the fluorinated phenylenediamine represented by the formula (2) is construed to include an acid adduct having an acid added to at least one of the diamines. Incidentally, since the acid adduct has considerable water solubility, the use of this compound in an aqueous solution proves a preferable mode of application. Meanwhile, the acid adduct can be removed by washing with an alkali substance. This compound excels in solubility in an organic solvent and is highly useful as a raw material for the synthesis of a macromolecular compound.

The alkalis which can be acted on the compound represented by the formula (7) include hydroxides, carbonates and phosphates of alkali metals and alkaline earth metals, ammonia, and amine, for example. In this invention, sodium hydroxide, potassium hydroxide, calcium hydroxide, sodium carbonate, sodium hydrogen carbonate, calcium carbonate, and an aqueous ammonia solution are particularly preferable.

The amount of the alkali to be used does not need to be particularly restricted but is only required to be sufficient for hydrolyzing the —NCO in the formula (7) into —$NH_2$. Generally, it is in the range of 1.8-6.0 mols, preferably 2.0-3.0 mols, per mol of the compound of the formula (7). The reason for this range is that the amount, when falling short of 1.8 mols, would possibly render the hydrolysis incomplete and lower the yield and, when exceeding 6.0 mols, would add to the amount of by-products formed.

In this invention, the action of the alkali on the compound of the formula (7) may be preferably carried out at a temperature exceeding 20° C. and not exceeding 100° C., more preferably in the range of 40-80° C., and particularly preferably 60-80° C. If this temperature falls short of 20° C., the rearrangement would be prevented from being completed or the rate of reaction is lowered, to impair the productivity. Conversely, if the temperature exceeds 100° C., the excess would possibly add to the amount of by-products formed and degrade the selectivity. The reaction time may be in the range of 0.5-3 hours, preferably 0.5-2 hours, and more preferably 1-1.5 hours.

The fluorinated phenylenediamine represented by the formula (2) which is consequently obtained may be isolated from the reaction solution and further purified. As means to effect this purification, distillation, recrystallization, sublimation, salting out, silica gel column chromatography, and treatment with an activated carbon may be cited. Since the by-products is generated only in a small amount in this invention, the purification can be carried out fully satisfactorily by such a simple operation as by the treatment with activated carbon.

In this invention, since the fluorinated phenylenediamine represented by the formula (2) is finally obtained by reacting the diamide represented by the formula (1) with NaOH and NaOX at a temperature in the range of 0-20° C. thereby obtaining the compound represented by the formula (3) and further treating this compound with an alkali at a temperature exceeding 20° C. and not exceeding 100° C., it means that the fluorinated phenylenediamine represented by the formula (2) can be produced simply and easily by incorporating the step of reacting the diamide represented by the formula (1) with NaOX at a NaOX/diamine ratio in the range of 2.0-6.0 and NaOH at a NaOH/diamide ratio in the range of 1.8-6.0 and by changing the temperature in two stages. In this respect, this invention relates tp a method for the production of a fluorinated phenylenediamine represented by the formula (2), which is characterized by incorporating therein a step of reacting a diamide represented by the formula (1) with NaOX at a NaOX/diamide ratio in the range of 2.0-6.0 and NaOH at a NaOH/diamide ratio in the range of 1.8-6.0, and by reacting the diamide with the NaOX and NaOH at a temperature in the range of 0-20° C. and subsequently heating the resultant reaction product to a temperature exceeding 20° C. and not exceeding 100° C.

By adjusting the temperature in the two stages as mentioned above, a fluorinated phenylenediamine represented by the formula (2) can be produced by an easy and simple method in a very high yield.

Thus, at the first stage, the reaction is performed at a temperature preferably in the range of 0-20° C., more preferably 0-10° C., and particularly preferably 0-5° C. and then at the second stage, the reaction is performed by heating at a temperature preferably exceeding 20° C. and not exceeding 100° C., more preferably falling in the range of 40-80° C., and particularly preferably 60-80° C. The first stage forms the —CONHX by the substitution of the X of the NaOX for the hydrogen atom of the amide (—$CONH_2$) of the formula (1) and, therefore, corresponds to the step of forming the compound of the formula (3). The reaction is performed at a temperature which is set so as to be not higher than 20° C. for the purpose of preventing the —CONHX, an extremely unstable group, from being decomposed and also be not lower than 0° C. for the purpose of preventing the reaction solution from freezing. The reaction time of the first stage may be in the range of 0.5-3.0 hours, preferably 0.5-2.0 hours, and more preferably 1.0-1.5 hours.

The second stage corresponds to the step of converting the —CONHX into the —NCO by the rearrangement and further converting the —NCO into the —NH$_2$ via the hydrolysis. As a result, the fluorinated phenylenediamine of the formula (2) would be formed from the compound of the formula (3). If the temperature falls short of 20° C., the rearrangement would be prevented from being completed or the rate of reaction would decrease, to impair the productivity. Conversely, if the temperature exceeds 100° C., the excess would possibly add to the amount of by-products formed and degrade the selectivity. The reaction time of the second stage may be in the range of 0.5-3.0 hours, preferably 0.5-2.0 hours, and more preferably 1.0-1.5 hours. According to this method, in the process for producing the fluorinated phenylenediamine represented by the formula (2) by using the compound of the formula (1) as the raw material, the target compound can be produced without isolating any intermediate. Moreover, in consequence of controlling the amount of NaOH to be used, the target compound can be produced in an extremely high yield.

Incidentally, the method of adjusting the temperature at the two stages as described above may be modified by adjusting the temperature at three stages or by gradually elevating the temperature. One modification may comprise performing the reaction at a temperature in the range of 0-20° C. for one hour, then at a temperature in the range of 20-60° C. for 0.5 hour, and further at a temperature in the range of 60-80° C. for one hour, for example.

After the reaction which follows the second stage of heating is completed, it is proper that the resultant reaction solution be adjusted to a pH in the range of 9-14 by the addition of an alkali. When the reaction solution is acid by the hydrolysis, the HX (wherein X is derived from the NaOX added during the reaction) in the reaction solution, for example, is linked as an acid adduct to the amino group of the fluorinated phenylenediamine represented by the formula (2). As a result, the compound obtained consequently becomes water-soluble. The acid adduct can be removed by adding an alkali to the compound and washing the compound with the alkali.

One of the characteristics of this invention is that the fluorinated phenylenediamine represented by the formula (2) as the target compound can be produced conveniently in a high yield without any separation of an intermediate by using the diamide represented by the formula (1) as the starting raw material and reacting the diamide with specific amounts of NaOX and NaOH. The fluorinated phenylenediamine of the formula (2) which is consequently obtained contains by-products only in a small amount and thus no subsequent steps of purifying the product to a high degree are not necessary. The fluorinated phenylenediamine represented by the formula (2) of this invention a molar absorption coefficient at a wavelength of 450 nm in a visible region, as measured with a spectrophotometer, preferably of not more than 2.5 (l/mol·cm), more preferably not more than 2.0 (l/mol·cm). The fluorinated phenylenediamine which is obtained by the method of production of this invention may be particularly useful as an optical material because it has a small molar absorption coefficient in a visible region.

The fluorinated phenylenediamine of the formula (2) so obtained may be isolated from the reaction solution and purified. The means for this purification includes distillation, recrystallization, sublimation, salting out, silica gel column chromatography, and treatment with an activated carbon, for example.

In this invention, polyamide can be produced by using as a raw material therefor the fluorinated phenylenediamine which is obtained by the method as described above. Though the method of production does not need to be particularly limited, polyamic acid represented by the formula (9) can be produced by reacting the fluorinated phenylenediamine obtained by the aforementioned method with tetracarboxylic acid represented by the following formula (8), the acid anhydride or acid chloride thereof, or the ester thereof in an organic solvent in accordance with the methods disclosed in Japanese Patent No. 3,082,879 and JP-A-2003-26,799, for example.

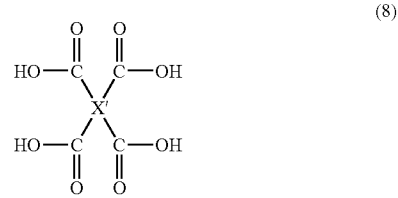

(8)

(wherein X' stands for a tetravalent organic group)

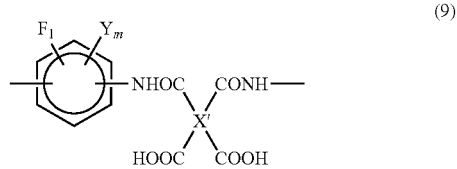

(9)

(wherein Y stands for H, Br, Cl, F, a $C_1$-$C_5$ alkyl group optionally having a substituent, or a $C_1$-$C_5$ alkoxyl group optionally having a substituent, l is an integer in the range of 1-4, m is an integer in the range of 0-3, provided that the total number of l and m (l+m) is 4, and X' stands for a tetravalent organic group).

For example, the reaction disclosed in JP-A-2003-26,799 may be performed under the same reaction conditions as specified therein while using the fluorinated phenylenediamine according to this invention in place of the 1,3-diaminobenzene derivative disclosed in JP-A-2003-26,799. Similarly, the reaction disclosed in Japanese Patent No. 3,082,879 while using the fluorinated phenylenediamine according to this invention in place of the diamine specified in Paragraph [0014] thereof.

As typical examples of the tetracarboxylic acid represented by the formula (8) and used advantageously herein, tetracarboxylic acids which are disclosed in Paragraphs [0040]-[0049] of JP-A-2003-26,799, in Paragraph [0013] of Japanese Patent No. 3,082,879, and in Paragraphs [0043]-[0046] of JP-A-2003-313,293 may be cited. These tetracaraboxylic acids, acid anhydrides or acid chlorides thereof, or esters thereof may be properly used. The typical examples of the substituent, "X'", in the formula (8) are as follows. To be specific, "X'" may stand for a tetravalent aliphatic organic group derived from cyclic alkyls, chain alkyls, olefins, and glycols; a tetravalent aromatic organic group derived from benzene biphenyl, biphenyl ether, bisphenyl benzene, and bisphenoxy benzene; and a tetravalent organic group such as halogen-containing aliphatic and aromatic organic groups. Among other substituents cited above, tetravalent aromatic organic groups, more preferably tetravalent halogen-containing aromatic organic groups are preferable as the "X'" in the formula (8). In these aromatic organic groups, particularly preferable tetravalent organic groups as the "X'" in the formula (8) are such tetravalent organic groups as represented by the following formulas.

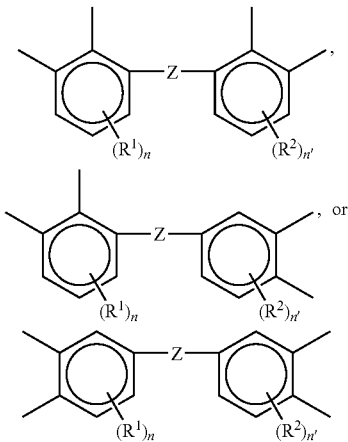

In the above formulas which represent the preferable organic groups as the "X'" in the formula (8), $R^1$ and $R^2$ stand for a halogen atom, namely a fluorine, chlorine, bromine, or iodine atom, preferably a fluorine or chlorine atom, and most preferably a fluorine atom. In this case, $R^1$ and $R^2$ may be identical with each other or different from each other. When a plurality of $R^1$'s and/or $R^2$'s are present in each the relevant benzene rings (namely, when n and/or n' is 2 or 3), they may be identical with each other or different from each other in the relevant benzene rings. Then, n and n' represent numbers of $R^1$ and $R^2$ bound to the relevant benzene rings and specifically are integers of in the range of 1-3. The integers, n and n', are preferably 3 because no C—H bonds are desirably present in consideration of such factors as the heat resistance, resistance to chemicals, water repellency, and low dielectric property. In this case, n and n' may be an identical number or different numbers.

In the formula as mentioned above, Z stands for a connector or a divalent group represented by the following formulas.

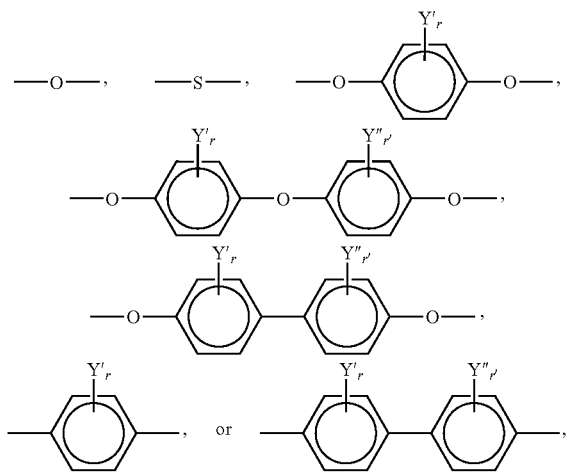

Among these Z's, Z preferably stands for a connector or a divalent groups represented by the following formulas.

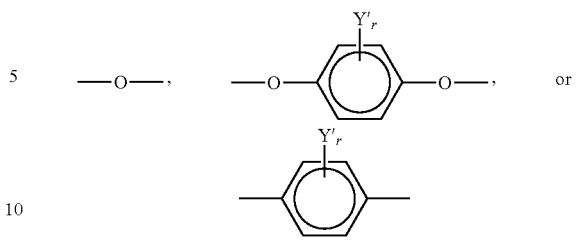

In the foregoing formulas representing the substituent "Z", Y', and Y" stand for a halogen atom, namely a fluorine, chlorine, bromine, or iodine atom, preferably a fluorine or chlorine atom, and most preferably a fluorine atom. When Y' and Y" are both present in the formula representing "Z", Y' and Y" may be identical with each other or different from each other. When Y' and Y" are respectively present in a plurality in the relevant benzene rings (namely, when r and/or r' is an integer of 2-4), each Y' and Y" may be identical with each other or different from each other. Then, r and r' respectively represent a number of Y' and Y" bound to the relevant benzene rings, respectively, and are integers in the range of 1-4, preferably 2-4. Most preferably, the integers, r and r', are preferably 4 because no C—H bonds are desirably present in consideration of such factors as the heat resistance, resistance to chemicals, water repellency, and low dielectric property. In this case, r and r' may be an identical number or different numbers.

Incidentally, the terminal of the polyamic acid contemplated by this invention is considered to be either an amine terminal or an acid derivative terminal, though it is variable with the amounts of the fluorinated phenylenediamine and the tetracarboxylic acid derivative to be added (molar ratio).

When the polyamic acid is cyclized by heating, the polyimide represented by the following formula (10) can be produced.

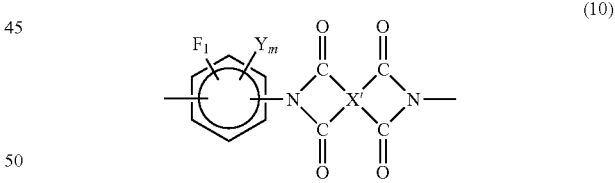

(10)

(wherein Y stands for H, Br, Cl, F, a $C_1$-$C_5$ alkyl group optionally having a substituent, or a $C_1$-$C_5$ alkoxyl group optionally having a substituent, l is an integer in the range of 1-4, m is an integer in the range of 0-3, provided that the total number of l and m (l+m) is 4, and X' stands for a tetravalent organic group).

The method of production thereof does not need to be particularly limited. The reaction in accordance with any of the methods disclosed in Japanese Patent No. 3,082,879, JP-A-2003-26,799, and JP-A-2003-313,293 can be carried out, for example. The terminal of the polyimide contemplated by this invention is considered to be an amine terminal or an acid derivative terminal.

Now, this invention will be described more specifically below with reference to working examples.

SYNTHESIS EXAMPLE 1

In a three neck flask having an inner volume of 1 liter, 63.08 g of purified water and 1048.74 g of 98% sulfuric acid were placed and stirred to prepare a 92% sulfuric acid solution. The resultant solution was heated to 80° C. and then kept cooled to keep the inner temperature of the flask in the range of 90 to 100° C. and 350.13 g (1.75 mols) of tetrafluoroisopthalonitrile was added piece meal to the cooled solution. After completion of this addition, the reaction solution in the flask was stirred for one hour while the inner temperature of the flask was kept at 90 to 100° C. and then the reaction solution was cooled to 30° C. Then, 1400 g of ice was placed in a beaker having an inner volume of 3 liters and the reaction solution was gently added dropwise to the ice so as to keep the inner temperature of the beaker from exceeding 60° C. After the completion of the dropwise addition, the mixture was cooled to 20° C. and then kept at 20° C. for one hour. A white solid which was precipitated was separated by filtration, washed with 1000 g of water, and then dried to obtain 407.95 g (1.73 mols) of tetrafluoroisophthalamide as a white solid (yield 98.8%).

SYNTHESIS EXAMPLE 2

By repeating the procedure of Synthesis Example 1 while using 757.92 g (3.5 mols) of 5-chloro-2,4,6-trifluoroisophthalonitrile in place of tetrafluoroisophthalonitrile, 876.45 g (3.47 mols) of 5-chloro-2,4,6-trifluoroisophthalamide was obtained as a white solid (yield 99.0%)

EXAMPLE 1

In a three neck flask having an inner volume of 1 liter, 197 g of water and 26.91 g (168.2 mmols) of 25% NaOH were placed and cooled to 0° C. Further, 83.53 g (280 mmols) of 24.95% NaClO was additionally placed in the flask and cooled to 0° C. Then, 16.7652 g (71 mmols) of tetrafluoroisophthalamide obtained in Synthesis Example 1 was gradually added to the flask. After the completion of the addition, the resultant mixture was stirred at a temperature of not higher than 5° C. for one hour. Then, the resultant reaction solution was diluted by the addition of 390 g of water, heated to 60-70° C. and stirred for one hour, and then cooled to 30° C. After the completion of cooling, the reaction solution was adjusted to pH 9 by the addition of 25% NaOH. This solution and 260 g of toluene added thereto were stirred together for 15 minutes for the sake of extraction. Thereafter, the resultant mixture was left standing for 10 minutes to effect the separation thereof. When the upper toluene layer was dried to a solid with an evaporator, 11.60 g of a reddish brown solid was obtained. This reddish brown solid and toluene were added together so as to give a total amount of 22.4 g and then heated to a temperature of not lower than 80° C. to completely dissolve the solid therein. The resultant solution was gradually cooled to 15° C. and then left standing at 15° C. for one hour. A brown solid consequently precipitated was separated by filtration, washed with 10 g of cold toluene, and then dried to obtain 7.94 g (44.1 mmols) of tetrafluoro-m-phenylenediamine as a brown solid (yield 63%). The purity of this product was determined by gas chromatography to find to be 99.99%.

EXAMPLE 2

In a three neck flask having an inner volume of 5 liters, 650 g of water and 153.6 g (960 mmols) of 25% NaOH were placed and cooled to 0° C. Further, 960.52 g (1600 mmols) of 12.40% NaClO was additionally placed and cooled to 0° C. Then, 95.65 g (405.1 mmols) of tetrafluoroisophthalamide obtained in Synthesis Example 1 was gradually added while the inner temperature of the flask kept at a level of not higher than 5° C. After the completion of the addition, the resultant mixture was stirred at a temperature of not higher than 5° C. for one hour. Then, the resultant reaction solution was diluted by the addition of 2210 g of water, heated to 60-70° C. and stirred for one hour, and cooled to 30° C. After the completion of the cooling, when the reaction solution was adjusted to pH 14 by the addition of 25% NaOH, a brown solid was precipitated. When the solid thus precipitated was separated by filtration, washed with purified water, and then dried, 54.4 g (302.1 mmols) of tetrafluoro-m-phenylenediamine was obtained as a brown solid (yield 75.5%). The purity of this product was determined by gas chromatography to find to be 99.99%.

EXAMPLE 3

In a three neck flask having an inner volume of 1 liter, 100 g of water and 23.07 g (144 mmols) of 25% NaOH were placed and cooled to 0° C. Further, 144.54 g (240 mmols) of 12.36% NaClO was placed additionally and cooled to 0° C. Then, 15.4171 g (61 mmols) of 5-chloro-2,4,6-trifluoroisophthalamide obtained in Synthesis Example 2 was gradually added while the inner temperature of the flask kept to below 5° C. After the completion of this addition, the resultant mixture was stirred at a temperature of not higher than 5° C. for one hour. Then, the resultant reaction solution was diluted by the addition of 345 g of water, heated to 60-70° C., stirred for one hour, and then cooled to 30° C. After the completion of the cooling, the reaction solution was adjusted to pH 9 by the addition of 25% NaOH. This solution and 260 g of toluene added thereto were stirred together for 15 minutes to effect the extraction. The resultant reaction solution was left standing for 10 minutes to effect the separation of the solution. When the upper toluene layer was dried to a solid with an evaporator, 10.61 g of a reddish brown solid was obtained. This reddish brown solid was added with toluene so as to give a total amount of 21.47 g and heated to a temperature of not lower than 80° C. to completely dissolve the solid therein. The resultant solution was gradually cooled to 15° C. and left standing at 15° C. for one hour. The brown solid consequently precipitated was separated by filtration, washed with 10 g of cold toluene, and dried to obtain 9.51 g (48.4 mmols) of 5-chloro-1,4,6-trifluoro-m-phenylenediamine as a brown solid (yield 80.7%). The purity of this product was determined by gas chromatography to find to be 99.81%.

EXAMPLE 4

0.3 g of tetrafluoro-m-phenylenediamine obtained in Example 1 was dissolved in acetonitrile so as to give a total amount of 3 g. When this solution was analyzed with a spectrophotometer to determine the absorbance in a visible region, the molar absorbance coefficient at a wavelength of 450 nm was found to be 1.649 (l/mol·cm).

EXAMPLE 5

A solution of 5 g of tetrafluoro-m-phenylenediamine obtained in Example 1 in 70 g of toluene and 0.15 g of activated carbon added thereto were stirred together at room temperature for one hour. After the completion of the stirring, the resultant mixture was filtered to separate the activated carbon therefrom. When the filtrate was dried to a solid with an evaporator, 4.64 g of tetrafluoro-m-phenylenediamine was obtained as a white solid. 0.3 g of this white solid was dissolved in acetonitrile to give a total amount of 3 g. When the solution was analyzed with a spectrophotometer to determine the absorbance in a visible region, the molar absorbance coefficient at a wavelength of 450 nm was found to be 0.013 (l/mol·cm).

EXAMPLE 6

0.3 g of 5-chloro-1,4,6-trifluoro-m-phenyleneidamine obtained in Example 2 was dissolved in acetonitrile to give a total amount of 3 g. When this solution was analyzed with a spectrophotometer to determine the absorbance in a visible region, the molar absorbance coefficient at a wavelength of 450 nm was found to be 1.802 (l/mol·cm).

EXAMPLE 7

A three neck flask having an inner volume of 50 ml was charged with 2.25 g (12.5 mmols) of tetraflfuoro-m-phenylenediamine obtained in Example 1, 7.28 g (12.5 mmols) of 4,4'-[(2,3,5,6-tetr4aflfuoro-1,4-phenylene)bis(oxy)]bis(3,5,6-trifluorophthalic anhydride), and 16 g of N,N-dimethylacetamide. This mixed solution was stirred in an atmosphere of nitrogen at room temperature for 30 minutes to form a homogeneous solution. The resultant solution was then left standing for four days to obtain a light yellow highly viscous polyamic acid solution.

EXAMPLE 8

A three neck flask having an inner volume of 50 ml was charged with 2.25 g (12.5 mmols) of tetrafluoro-m-phenylenediamine obtained in Example 5, 7.28 g (12.5 mmols) of 4,4'-[(2,3,5,6-tetrafluoro-1,4-phenylene)bis(oxy)]bis(3,5,6-trifluorophthalic anhydride), and 16 of N,N-dimethyl acetamide. The resultant mixed solution was stirred in an atmosphere of nitrogen at room temperature for 30 minutes to form a homogeneous solution. The resultant solution was further left standing for four days to obtain a light yellow highly viscous polyamic acid solution.

EXAMPLE 9

A three neck flask having an inner volume of 50 ml was charged with 2.46 g (12.5 mmols) of 5-chloro-2,4,6-trifluoro-m-phenylenediamine obtained in Example 3, 7.28 g (12.5 mmols) of 4,4'-[(2,4,5,6-tetrafluoro-1,4-phenylene)bis(oxy)] bis(3,5,6-trifluorophthalic anhydride), and 16 g of N,N-dimethyl acetamide. The resultant mixed solution was stirred in an atmosphere of nitrogen at room temperature for 30 minutes to form a homogeneous solution. This solution was further left standing for four days to obtain a light yellow highly viscous polyamic acid solution.

EXAMPLE 10

The polyamic acid obtained in Example 7 was applied by spin coating on a silicon substrate having a diameter of 4 inches. When the coating was heated in an atmosphere of nitrogen at 70° C. for two hours, at 160° C. for one hour, at 250° C. for 30 minutes, and further at 350° C. for one hour, a polyimide film was formed on the silicon substrate.

EXAMPLE 11

The polyamic acid obtained in Example 8 was applied by spin coating on a silicon substrate having a diameter of 4 inches. When the coating was heated in an atmosphere of nitrogen at 70° C. for two hours, at 160° C. for one hour, at 250° C. for 30 minutes, and further at 350° C. for one hour, a polyimide film was formed on the silicon substrate.

EXAMPLE 12

The polyamic acid obtained in Example 9 was applied by spin coating on a silicon substrate having a diameter of 4 inches. When the coating was heated in an atmosphere of nitrogen at 70° C. for two hours, at 160° C. for one hour, at 250° C. for 30 minutes, and further at 350° C. for one hour, a polyimide film was formed on the silicon substrate.

COMPARATIVE EXAMPLE 1

In a three neck flask having an inner volume of 50 ml, 4.0 g (101.84 mmols) of sodium hydroxide and 25 ml of deionized water were placed. Then, 1.09 ml (21.18 mmols) of bromine was added dropwise to the flask over a period of 15 minutes while the flask kept cooled with an ice bath. Then, 2.0 g (8.47 mmols) of tetrafluoroisophthalamide was additionally placed. The resultant mixed solution was refluxed and stirred for 20 hours, cooled to room temperature, then extracted with isopropyl ether, washed with deionized water, then dried over magnesium sulfate, and distilled to expel the solvent with an evaporator to obtain 2.42 g of a brown solid. In a three neck flask having an inner volume of 50 ml, this solid and 20 mg of 20% hydrochloric acid were placed together, refluxed and stirred for five hours. The solution was cooled to room temperature. In a beaker having an inner volume of 500 ml, ice water was placed and the cooled solution was poured into the ice water and then an aqueous sodium hydroxide solution was added there to dropwise till the pH value reached 14. Then, the resultant reaction solution was extracted with chloroform, washed with deionized water, dried over magnesium sulfate, and distilled to expel the solvent with an evaporator to obtain 0.25 g of a reddish brown solid (yield 16.4%).

0.1 g of tetrafluoro-m-phenylenediamine thus obtained was dissolved in acetonitrile so as to give a total amount of 1 g. When the solution was analyzed with a spectrophotometer to determine the absorbance in a visible region, the molar absorption coefficient at a wavelength of 450 nm was found to be 4.124 (l/mol·cm).

COMPARATIVE EXAMPLE 2

The solution of 0.15 g of tetrafluoro-m-phenylenediamine obtained in Comparative Example 1 in 2.1 g of toluene and 0.0045 g of activated carbon added thereto were stirred together at room temperature for one hour. After the completion of the stirring, the resultant mixture was filtered to remove the activated carbon. When the filtrate was dried to a solid with an evaporator, 0.13 g of tetrafluoro-m-phenylenediamine was obtained as a brown solid. 0.13 g of this brown solid was dissolved in acetonitrile so as to give a total amount of 1.3 g. When this solution was analyzed with a spectrophotometer to determine the absorbance in a visible region, the molar absorption coefficient at a wavelength of 450 nm was found to be 3.093 (L/mol-cm).

COMPARATIVE EXAMPLE 3

The reaction of Hoffmann rearrangement was tried by following the procedure of Example 1 while using 41.79 g (140 mmols) of 24.95% NaClO in place of 83.53 g (280 mmols) of 24.95% NaClO. As a result, 0.54 g (3 mmols, yield 4.3%) of tetrafluoro-m-phenylenediamine was obtained. The purity of this product was determined by gas chromatography to find to be 98.30%.

INDUSTRIAL APPLICABILITY

This invention is to provide a fluorinated phenylenediamine manifesting low absorption in a visible region and suitable for an optical material, polyamic acid using the diamine as a raw material, and a method for the convenient production of polyimide. The products according to this invention are useful for the production of an optical material.

The invention claimed is:

1. A method for the production of a fluorinated phenylenediamine represented by the following formula (2), which comprises a step of reacting a diamide represented by the following formula (1) with NaOX [wherein X stands for a bromine atom (Br) or a chlorine atom (Cl)] at a molar ratio of the NaOX to the diamide (NaOX/diamide ratio) in the range of 3.0-6.0 and NaOH at a molar ratio of the NaOH to the diamide (NaOH/diamide ratio) in the range of 1.8-4.0,

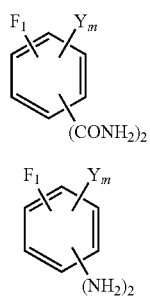

wherein in the formulas (1) and (2), Y stands for a hydrogen atom (H), a bromine atom (Br), a chlorine atom (Cl), a fluorine atom (F), a C1-C5 alkyl group optionally having a substituent, or a C1-C5 alkoxyl group optionally having a substituent, l is an integer in the range of 1-4, m is an integer in the range of 0-3, provided that the total number of l and m (l+m) is 4; and, upon completion of the reaction, adding an alkali to adjust the pH of the solution to be in the range of 9 to 14.

2. A method according to claim 1, wherein said diamide is reacted with NaOX and NaOH at a temperature in the range of 0-20° C. and the resultant reaction product is heated at a temperature exceeding 20° C. and not exceeding 100° C.

3. A method according to claim 1, wherein said diamide is a diamide represented by the following formula (4) and said phenylenediamine is a phenylenediamine represented by the following formula (5),

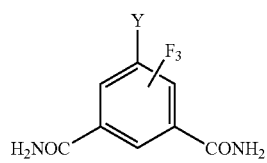

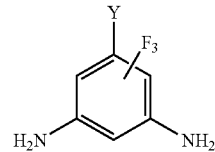

wherein in the formulas (4) and (5), Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent.

4. A method according to claim 1, wherein the molar absorption coefficient of the fluorinated phenylenediamine represented by the formula (2) at a wavelength of 450 nm is not more than 2.5 (l/mol·cm).

5. A method for the production of a polyamic acid represented by the formula (9), which comprises the steps of:

producing a fluorinated phenylenediamine represented by the formula (2) by reacting a diamide represented by the formula (1) with NaOX [wherein X stands for a bromine atom (Br) or a chlorine atom (Cl)] at a molar ratio of the NaOX to the diamide (NaOX/diamide ratio) in the range of 3.0-6.0 and NaOH at a molar ratio of the NaOH to the diamide (NaOH/diamide ratio) in the range of 1.8-4.0, and after the reaction, adding an alkali to adjust the resultant reaction solution pH to be in the range of 9 to 14; and reacting the fluorinated phenylenediamine with tetracarboxylic acid represented by the formula (8), the acid anhydride or acid chloride thereof or the ester thereof in an organic solvent,

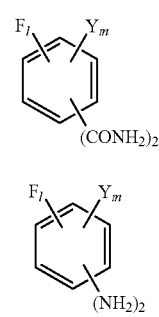

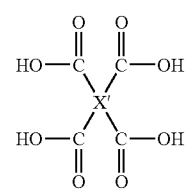

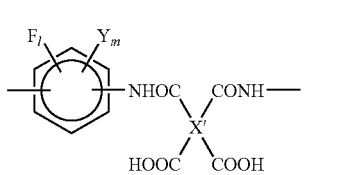
(9)

wherein Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent, l is an integer in the range of 1-4, m is an integer in the range of 0-3, provided that the total number of l and m (l+m) is 4, and X' stands for a tetravalent organic group.

6. A method for the production of polyimide represented by the formula (10), which comprises the steps of:

producing a fluorinated phenylenediamine represented by the formula (2) by reacting a diamide represented by the formula (1) with NaOX [wherein X stands for a bromine atom (Br) or a chlorine atom (Cl)] at a molar ratio of the NaOX to the diamide (NaOX/diamide ratio) in the range of 3.0-6.0 and NaOH at a molar ratio of the NaOH to the diamide (NaOH/diamide ratio) in the range of 1.8-4.0, and after the reaction, adding an alkali to adjust the resultant reaction solution pH to be in the range of 9 to 14; and producing a polyamic acid represented by the formula (9) by reacting the fluorinated phenylenediamine with tetracarboxylic acid represented by the formula (8), the acid anhydride or acid chloride thereof, or the ester thereof in an organic solvent; and cyclizing by heating the polyamic acid,

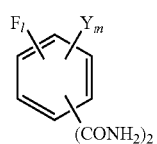
(1)

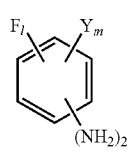
(2)

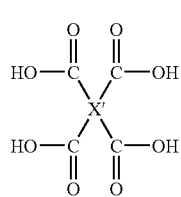
(8)

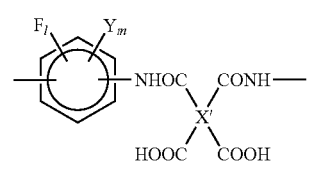
(9)

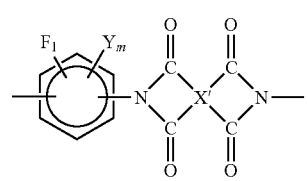
(10)

wherein Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent, l is an integer in the range of 1-4, m is an integer in the range of 0-3, provided that the total number of l and m (l+m) is 4, and X' stands for a tetravalent organic group.

7. A method according to claim 2, wherein said diamide is a diamide represented by the following formula (4) and said phenylenediamine is a phenylenediamine represented by the following formula (5)

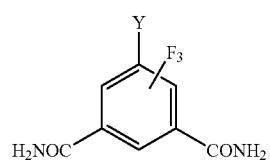
(4)

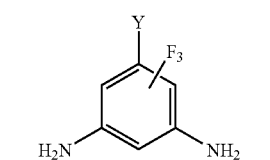
(5)

wherein in the formulas (4) and (5), Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent.

8. A method according to claim 2, wherein the molar absorption coefficient of the fluorinated phenylenediamine represented by the formula (2) at a wavelength of 450 nm is not more than 2.5 (l/mol·cm).

9. A method according to claim 3, wherein the molar absorption coefficient of the fluorinated phenylenediamine represented by the formula (2) at a wavelength of 450 nm is not more than 2.5 (l/mol·cm).

10. A method according to claim 7, wherein the molar absorption coefficient of the fluorinated phenylenediamine represented by the formula (2) at a wavelength of 450 nm is not more than 2.5 (l/mol·cm).

11. A method for the production of a polyamic acid represented by the formula (9), which comprises the steps of:

producing a fluorinated phenylenediamine represented by the formula (2) by reacting a diamide represented by the formula (1) with NaOX [wherein X stands for a bromine atom (Br) or a chlorine atom (Cl)] at a molar ratio of the NaOX to the diamide (NaOX/diamide ratio) in the range of 3.0-6.0 and NaOH at a molar ratio of the NaOH to the diamide (NaOH/diamide ratio) in the range of 1.8-4.0, at a temperature in the range of 0-20° C., heating the resultant reaction product subsequently at a temperature exceeding 20° C. and not exceeding 100° C., and, upon completion of the reaction, adding an alkali to adjust the pH of the solution to be in the range of 9 to 14; and reacting the fluorinated phenylenediamine produced with tetracaraboxylic acid represented by the formula (8), the acid anhydride or acid chloride thereof, or the ester thereof in an organic solvent,

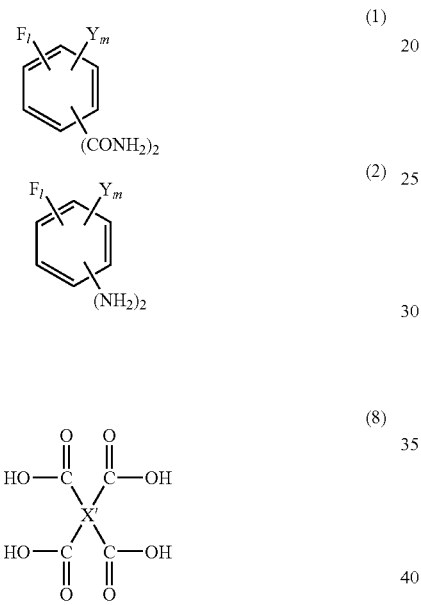

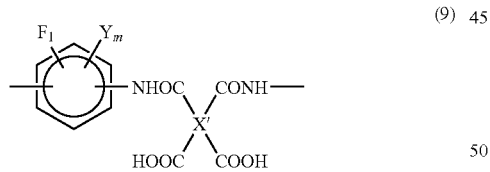

wherein Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent, l is an integer in the range of 1-4, m is an integer in the range of 0-3, provided that the total number of l and m (l+m) is 4, and X' stands for a tetravalent organic group.

12. A method for the production of polyimide represented by the formula (10), which comprises the steps of:

producing a fluorinated phenylenediamine represented by the formula (2) by reacting a diamide represented by the formula (1) with NaOX [wherein X stands for a bromine atom (Br) or a chlorine atom (Cl)] at a molar ratio of the NaOX to the diamide (NaOX/diamide ratio) in the range of 3.0-6.0 and NaOH at a molar ratio of the NaOH to the diamide (NaOH/diamide ratio) in the range of 1.8-4.0, at a temperature in the range of 0-20° C., heating the resultant reaction product subsequently at a temperature exceeding 20° C. and not exceeding 100° C., and, upon completion of the reaction, adding an alkali to adjust the pH of the solution to be in the range of 9 to 14; and producing a polyamic acid represented by the formula (9) by reacting the fluorinated phenylenediamine with tetracaraboxylic acid represented by the formula (8), the acid anhydride or acid chloride thereof or the ester thereof in an organic solvent; and cyclizing by heating the polyamic acid,

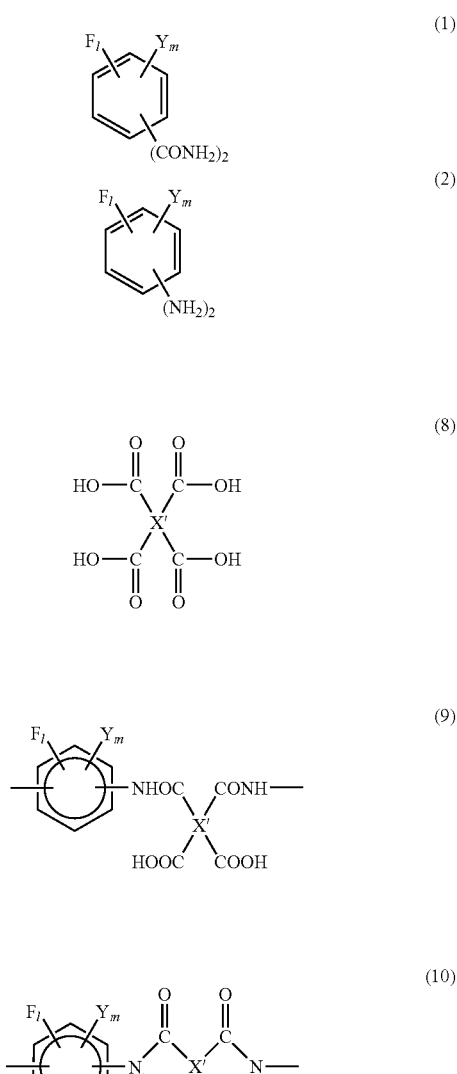

wherein Y stands for a hydrogen atom (H), a bromine atom (Br), a chlorine atom (Cl), a fluorine atom (F), a $C_1$-$C_5$ alkyl group optionally having a substituent, or a $C_1$-$C_5$ alkoxyl group optionally having a substituent, l is an integer in the range of 1, m is an integer in the range of 0-3, provided that the total number of l and m (l+m) is 4, and X' stands for a tetravalent organic group.

13. A method according to claim 1, wherein l is 3 or 4 and m is 0 or 1.

14. A method according to claim 5, wherein l is 3 or 4 and m is 0 or 1.

15. A method according to claim 6, wherein l is 3 or 4 and m is 0 or 1.

16. A method according to claim 11, wherein l is 3 or 4 and m is 0 or 1.

17. A method according to claim 12, wherein l is 3 or 4 and m is 0 or 1.

* * * * *